United States Patent
Aggerholm et al.

(10) Patent No.: US 9,409,001 B2
(45) Date of Patent: Aug. 9, 2016

(54) MEDICAL BALLOON WITH PARTICLES THEREIN

(71) Applicant: Cook Medical Technologies LLC, Bloomington, IN (US)

(72) Inventors: Steen Aggerholm, St. Heddinge (DK); Anders Scheel Klausen, Naestved (DK); Thomas Lysgaard, Solroed Strand (DK); Anne-Mette Hoppe Sönnichsen, Soroe (DK); Allan Torp, Bjaeverskov (DK)

(73) Assignee: Cook Medical Technologies LLC, Bloomington, IN (US)

( * ) Notice: Subject to any disclaimer, the term of this patent is extended or adjusted under 35 U.S.C. 154(b) by 100 days.

(21) Appl. No.: 13/786,690

(22) Filed: Mar. 6, 2013

(65) Prior Publication Data
US 2013/0261548 A1   Oct. 3, 2013

(30) Foreign Application Priority Data

Mar. 27, 2012 (GB) .................................. 1205367.4

(51) Int. Cl.
*A61M 29/00* (2006.01)
*A61M 25/10* (2013.01)
(Continued)

(52) U.S. Cl.
CPC .............. *A61M 25/10* (2013.01); *A61L 29/126* (2013.01); *A61L 29/18* (2013.01); *A61M 25/1029* (2013.01); *A61M 25/1027* (2013.01);
(Continued)

(58) Field of Classification Search
CPC ............ A61M 25/10; A61M 25/1027; A61M 25/1029; A61M 2025/1031; A61M 2025/1043; A61M 2025/1075; A61M 2025/1086

USPC .......................................................... 606/191
See application file for complete search history.

(56) References Cited

U.S. PATENT DOCUMENTS

| 5,081,997 A | * | 1/1992 | Bosley et al. ................. 600/458 |
| 5,289,831 A | * | 3/1994 | Bosley .................... A01K 85/00 128/899 |
| 5,290,306 A | | 3/1994 | Trotta et al. |

(Continued)

FOREIGN PATENT DOCUMENTS

| EP | 2 561 898 A1 | 2/2013 |
| WO | WO 97/27894 | 8/1997 |

(Continued)

OTHER PUBLICATIONS

Communication from EPO with European Search Report and Annex for corresponding European Patent Application No. EP 13 27 5052, dated Aug. 13, 2013, 8p.

(Continued)

*Primary Examiner* — Robert Lynch
(74) *Attorney, Agent, or Firm* — Brinks Gilson & Lione

(57) ABSTRACT

A balloon catheter includes a balloon having a plurality of layers. The inner layer acts as a support layer to the outer layer. Embedded within the outer layer is a plurality of particles or pellets which in one embodiment provide roughening of the outer surface of the balloon. The particles or pellets, particularly in conjunction with an inner support layer, ensure maintenance of the roughened outer surface of the balloon during inflation of the balloon. In another embodiment, the particles or pellets may be radiopaque and/or echogenic with or without creating surface roughening of the balloon.

16 Claims, 5 Drawing Sheets

(51) Int. Cl.
*A61L 29/12* (2006.01)
*A61L 29/18* (2006.01)
(52) U.S. Cl.
CPC .................. *A61M2025/1031* (2013.01); *A61M 2025/1075* (2013.01); *A61M 2025/1086* (2013.01)

(56) References Cited

U.S. PATENT DOCUMENTS

| | | |
|---|---|---|
| 6,258,099 B1 | 7/2001 | Mareiro et al. |
| 6,786,889 B1 | 9/2004 | Musbach et al. |
| 7,758,572 B2 | 7/2010 | Weber et al. |
| 2001/0039395 A1 | 11/2001 | Mareiro et al. |
| 2003/0004535 A1 | 1/2003 | Musbach et al. |
| 2003/0055449 A1 | 3/2003 | Lee et al. |
| 2003/0114915 A1 | 6/2003 | Mareiro et al. |
| 2005/0215885 A1 | 9/2005 | Lee et al. |
| 2005/0261670 A1 | 11/2005 | Weber et al. |
| 2005/0271844 A1 | 12/2005 | Mapes et al. |
| 2007/0100279 A1 | 5/2007 | Bates |
| 2007/0142772 A1 | 6/2007 | Deshmukh et al. |
| 2008/0021495 A1 | 1/2008 | Lee et al. |
| 2010/0130926 A1 | 5/2010 | Lee et al. |
| 2011/0022152 A1 | 1/2011 | Grandt |
| 2011/0160659 A1 | 6/2011 | Clarke et al. |
| 2012/0065586 A1 | 3/2012 | Lee et al. |
| 2013/0030410 A1* | 1/2013 | Drasler et al. ............... 604/510 |
| 2013/0053770 A1 | 2/2013 | Aggerholm et al. |
| 2014/0081310 A1 | 3/2014 | Lee et al. |

FOREIGN PATENT DOCUMENTS

| | | | |
|---|---|---|---|
| WO | WO 03/035161 A1 * | 5/2003 | ........... A61M 25/10 |
| WO | WO 2009/080320 A1 | 7/2009 | |
| WO | WO 2010/033231 A2 | 3/2010 | |

OTHER PUBLICATIONS

Combined Search and Examination Report for corresponding Great Britain Patent Application No. GB 1205367.4, dated Jul. 31, 2012, 4p.

Extended European Search Report for corresponding Great Britain Patent Application No. EP 13158957.4, dated Sep. 21, 2015, 6p.

Examination Report for corresponding Great Britain Patent Application No. GB 1205367.4, dated Mar. 16, 2016, 2p.

* cited by examiner

MEDICAL BALLOON WITH PARTICLES THEREIN

CROSS-REFERENCE RELATED APPLICATIONS

This application claims priority to GB application no. 1205367.4, filed Mar. 27, 2012, titled "Medical Balloon with Particles Therein," the contents of which are incorporated herein by reference.

TECHNICAL FIELD

The present invention relates to medical balloons and to balloon catheters.

BACKGROUND ART

The use of medical balloons and balloon catheters is gaining widespread use in the medical field for effecting a variety of medical procedures, such as angioplasty, vascular dilatation, valvuloplasty, vascular occlusion, deployment and retrieval of implantable medical devices and for other clinical applications. There are a number of technical and clinical considerations involved with the design and use of medical balloons including, for example, visibility of the balloon during the medical procedure and also maintaining the position of the balloon in the patient's vasculature. Such medical balloons are typically made of a thin-walled material in order to ensure that the balloon can be wrapped to a very small profile and also to optimize the flexibility of the balloon. As a result of this, medical balloons of this nature tend to be very difficult to see by conventional imaging techniques when they are located within a patient. In light of this, it is known to inflate such medical balloons with an imaging agent, typically a radiopaque material. However, such materials tend to be relatively viscous compared to traditional inflating fluids, such as saline solution, resulting in greater inflating and deflation times of the balloon and also restricting the size of the inflation/deflation lumen which can be used for that balloon. Moreover, these radiopaque fluids tend not to be particularly biocompatible, leading to potential difficulties should the balloon burst and release fluid into the patient's blood system.

With respect to positioning of the balloon within the patient's vasculature, since medical balloons are typically inflated until they are fully stretched, they tend to have a smooth outer surface. The result of this is that they tend to be relatively slippery. A slippery balloon can be difficult to position accurately and to hold in position within a patient's vasculature, particularly given the fluid pressure within a patient's vessel. Migration of the balloon can lead to medical complications. Attempts have been made to roughen the outer surface of a medical balloon. However, these attempts have not always been successful as surface features tend to flatten as the balloon is stretched during its inflation.

Examples of balloon catheters can be found in U.S. Pat. No. 7,758,572 and US 2010/0130926.

DISCLOSURE OF THE INVENTION

The present invention seeks to provide an improved medical balloon and balloon catheter.

According to an aspect of the present invention, there is provided a medical balloon for endoluminal location within a patient, the balloon including a first balloon layer made of a polymeric material, and a second balloon layer overlying the first balloon layer, which second balloon layer includes a polymeric material within which there are included generally round or cuboidal particles therewithin.

The particles in one embodiment create a roughened outer surface to the balloon. In another embodiment, the particles are radiopaque and/or echogenic. It will be appreciated that the particles may both create roughening and be radiopaque/echogenic.

This structure of balloon includes the advantageous functionality provided by the particles without compromising the performance characteristics of the balloon, in particular its strength and pliability. The provision of an inner layer of polymeric material, which preferably includes no particulate additive, provides strength to the balloon, with the outer layer providing a roughened and/or visible layer. In the case where the particles provide a roughened surface, the inner layer acts as a support which in practice avoids flattening of the roughening features provided by the particles. In the case where the particles provide echogenicity and/or radiopacity, the inner layer similarly provides a support structure to the outer layer, which would otherwise be weaker than a layer which does not have particulate additive. This structure of support layer and outer functional layer retains balloon strength without requiring a large increase in balloon wall thickness.

Advantageously, the particles are generally spherical or cuboidal.

In the preferred embodiment, the particles have a diameter of between 2 to 20 micrometres, more preferably, a diameter of between 5 to 10 micrometres and most preferably a diameter of around 7 micrometres.

Advantageously, the first balloon layer has a thickness in the range of around 0.01 millimetres to around 0.10 millimetres. The second balloon layer may have a thickness in the range of around 0.005 millimetres to around 0.05 millimetres.

Where the particles provide surface roughness, the outer surface of the balloon preferably has a roughness of 0.2 to 18 Ra.

Preferably, the particles are provided at a density of about 50 to about 80% by weight or about 3 to about 5% by volume of the second layer of the balloon.

In a practical embodiment, the particles are made of a material having a higher softening or melting temperature compared to the softening or melting temperature of the polymeric material of the second balloon layer. They may be made of a material having a higher softening or melting temperature than the softening or melting temperature of the polymeric material of the first balloon layer.

Advantageously, the particles are made of a material having a higher Durometer compared to the Durometer of the polymeric material of the second balloon layer.

In the preferred embodiment, the particles are made of one or more of: glass, metal, a polymer, ceramic, tungsten, carbon and other similar materials.

The polymeric material of the first balloon layer may include one or more of: polyamide (nylon), polyether block amide (for instance Pebax[RTM]), PET, polyethylene and polyurethane. The polymeric material of the second balloon layer preferably has a lower softening or melting temperature than the softening or melting temperature of the material of the first balloon layer.

Advantageously, the second balloon layer covers the entirety of an inflatable portion of the balloon and may also cover end and neck portions of the balloon. The first and second balloon layers may be co-extruded, fused or bonded to one another.

The particles may be of a radiopaque and/or echogenic material.

According to another aspect of the present invention, there is provided a medical balloon provided with a first balloon layer made of a polymeric material, and a second balloon layer overlying the first balloon layer, which second balloon layer includes a polymeric material within which there are included generally rounded, spherical or cuboidal particles therewithin, said particles creating a roughened outer surface to the balloon; said balloon being for use in one of angioplasty, occlusion, dilatation, valvuloplasty, and deployment of a medical device.

According to another aspect of the present invention, there is provided a method of making a medical balloon, the balloon including a first balloon layer made of a polymeric material, and a second balloon layer overlying the first balloon layer, which second balloon layer includes a polymeric material within which there are included generally round, spherical or cuboidal particles therewithin, the method including the steps of: providing a raw tubing having a first layer of the polymeric material and a second layer overlying the first layer and formed of a polymeric material; providing said particles; providing a mold for forming the balloon from said raw tubing; providing an inflation mechanism for inflating the raw tubing; providing a heating mechanism for heating the raw tubing; disposing in the mold the raw tubing; operating the mold, heating and inflation mechanisms, thereby to cause the raw tubing to inflate within the mold, wherein the second layer of the tubing softens or melts to reflow, said particles being embedded in the outer surface of the balloon.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
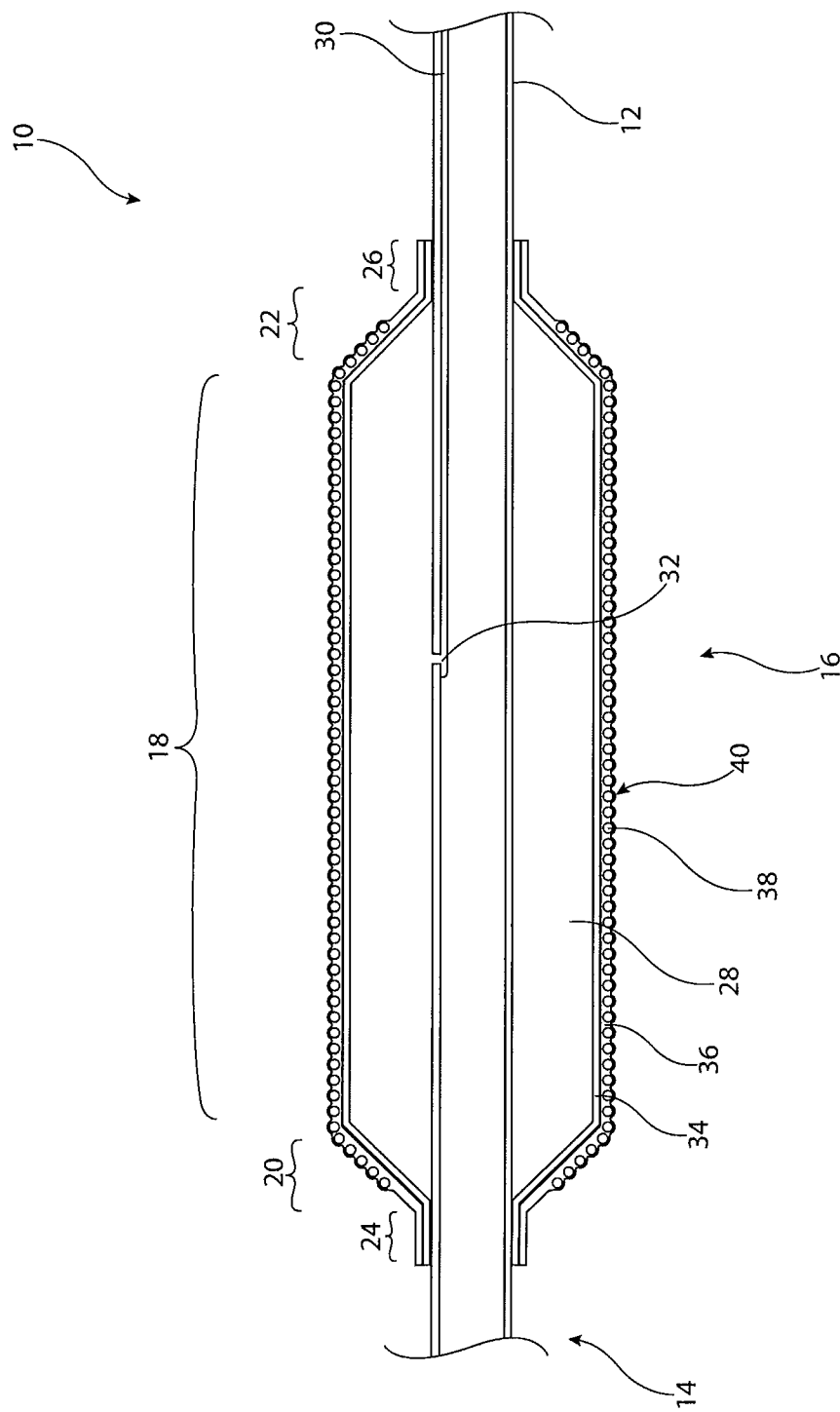
FIG. 1 is a side elevational view, in cross-section, of an embodiment of medical balloon and balloon catheter.

It is to be understood that the drawings are schematic only and are not to scale. They are of a form which is intended to facilitate the understanding of the teachings herein. As a result, similar features, such as layers of the balloon, are not necessarily of the thicknesses or relative thicknesses as appear in the drawings but may be different. For instance, the outer layer of the balloons shown in the drawings and described below in practice is likely to be much thinner than depicted and in particular thinner than the underlying layer of polymeric material.

In the embodiments shown in the drawings and described below, the medical balloon is shown as being made of two layers, an inner layer and an outer layer. Whilst this is the preferred arrangement for the medical balloon, the teachings herein are not limited to a balloon having two layers only and could, for instance, be formed of a plurality of layers and also to include additional features, such as strengthening elements, strengthening sleeves, scoring elements and so on.

Similarly, even though the embodiments of medical balloon depicted in the drawings and described below have body portions which are substantially cylindrical, this is only for the purpose of illustration. The teachings herein apply to medical balloons having a variety of shapes including, for example, hourglass shape, wedge-shape and so on. The shape of the balloon is not relevant to the teachings herein.

Referring first to FIG. 1, there is shown a first embodiment of balloon catheter 10 which includes a catheter 12 of substantially conventional form and which has a distal end 14, typically terminated with a dilator tip. The catheter 12 also has a proximal end which is typically coupled to an external manipulation unit, which includes one or more haemostatic valves, one or more ports for the supply of inflation fluid, flushing fluid and so on. These elements of the balloon catheter are known in the art and therefore not described in detail herein.

Fixed to the catheter 12 is a medical balloon 16 which in this embodiment includes a substantially cylindrical body portion 18 bounded at either end by conical end portions 20, 22, the latter terminating in neck portions 24, 26. The neck portions 24, 26 are fixed in fluid tight manner to the catheter 12. The medical balloon 16 has an internal chamber 28, in practice defined by the interior surface of the balloon 16 and the exterior surface of the catheter 12.

The catheter 12 includes a lumen 30 for the provision of inflation fluid into the chamber 28, for which purpose the catheter 12 is provided with a port 32 at a distal end of the inflation lumen 30 which couples to the chamber 28.

In FIG. 1, the medical balloon 16 is shown in an inflated condition. The balloon 16 is able to deflate by withdrawal of inflation fluid from the chamber 28, and typically to be wrappable round the catheter 12 for delivery and removal purposes, again as is known in the art. For this purpose, the balloon 16 may have a non-stretched configuration in which it will at least partially fold to assist in its wrapping around the catheter 12.

In this embodiment, the balloon 16 has first and second layers 34, 36. These layers 34, 36 are bonded or otherwise integral with one another so that they move in unitary manner. The first or inner balloon layer 34 is made of a polymeric material, which may be any of the conventionally known materials, including, for example, a polyamide (nylon), polyurethane, a polyether block amide such as Pebax™, polyethylene, PET and the like. The inner layer 34 of the balloon 16 is preferably made of a non-conformable material, that is which does not exhibit substantial stretching at normal operating pressures of the balloon 16. In other embodiments, though, the inner layer 34 could be made of a conformable material.

In the preferred embodiment, the inner layer 34 includes no particulate material and is most preferably made purely of one or more polymeric materials. This enables the inner layer 34 to be of optimum strength and thus to be made as thin as possible. The addition of other elements, in particular particulate materials can reduce the strength of the layer, thus leading to the need for thickening of the layer. The inner layer 34 is substantially smooth, that is has substantially smooth inner and outer surfaces. It will be appreciated also, that the balloon 16 is substantially tubular in form with a cylindrical body portion 18.

The outer layer 36, which in this example overlies the inner layer 34 for the entirety of the length of the balloon 16, has embedded therewithin generally round, spherical or cuboidal particles 38, described in further detail below. The outer layer 36 has a substantially smooth inner surface which is, preferably, entirely bonded or otherwise integral with the outer surface of the inner layer 34 and is thus substantially smooth. The outer surface 40 of the outer layer 36, however, is roughened as a result of the presence of the particles 38 in the layer 36. Thus, as can be seen in FIG. 1, the balloon 16 has a roughened outer surface. This, as will be described in further detail below, gives the balloon better positioning characteristics within a patient able to reduce the risk of migration of the balloon catheter 10 when deployed in a patient.

The outer layer 36 of the balloon 16 can be made of a variety of materials, including the same materials as of the inner layer 34. It is preferred that the outer layer 36 is made of a material which has a lower softening or melting temperature than that of the inner layer 34, for purposes which are explained below. The outer layer could be termed a reflow layer. In addition, it is preferred that the particles 38 are made of a material which has a higher softening or melting temperature than the softening or melting temperature of the material of the second layer 36 and preferably also of the inner layer 34. In the preferred embodiments, the particles 38 may be made of glass, metal, ceramic, or tungsten or carbon or the like to provide radiopacity.

Figure 2:
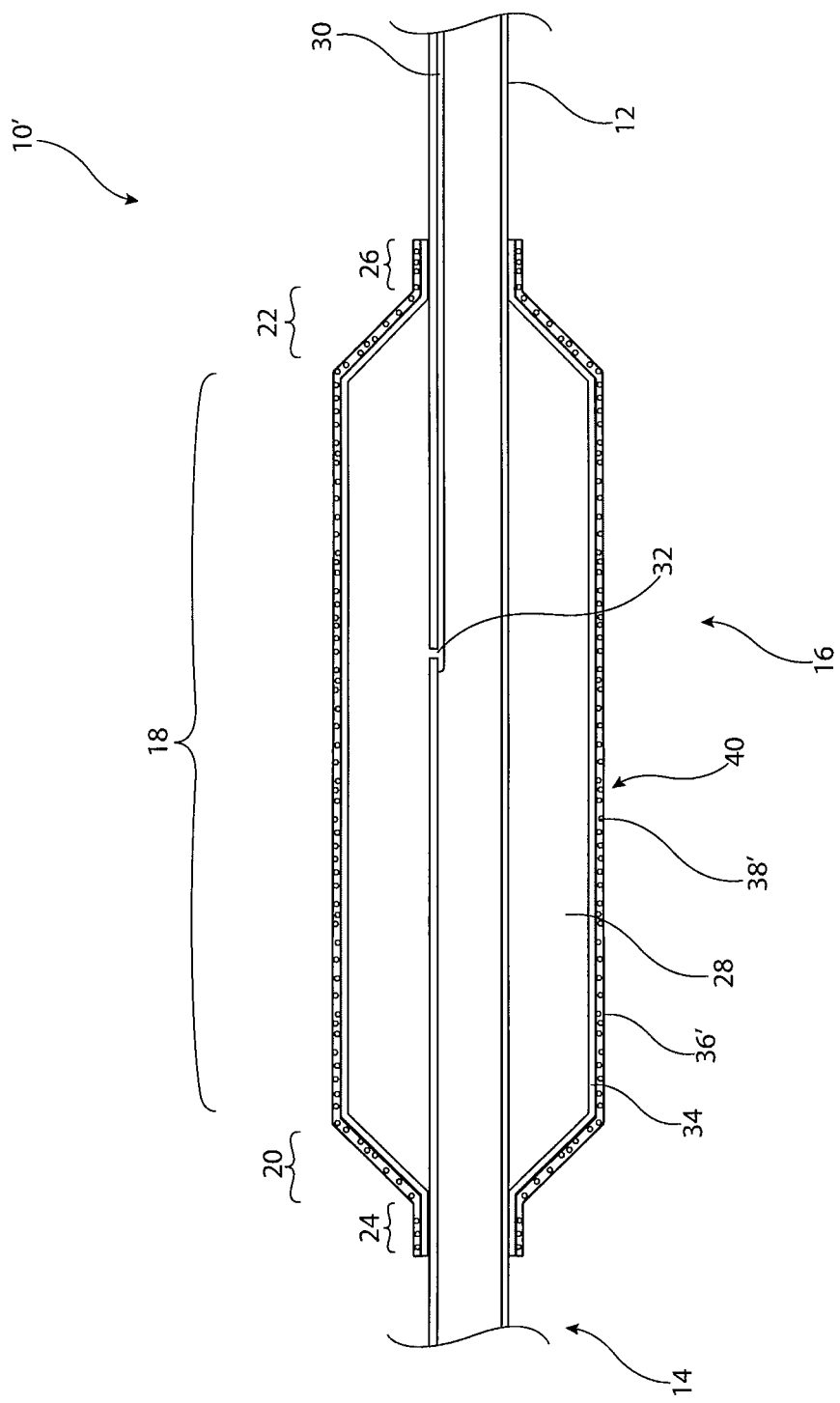
FIG. 2 is a side elevational view, in cross-section, of another embodiment of medical balloon and balloon catheter.

The embodiment of FIG. 1 provides a balloon 16 which has a roughened outer surface. A different embodiment is shown in FIG. 2, in which the balloon 16' is equally formed of inner and outer layers, in which the inner layer 34 is analogous to the layer 34 of the balloon 16 of FIG. 1. The outer layer 36', however, has a smooth outer surface and has embedded therewithin particles 38', again generally round, spherical or cuboidal. In this embodiment, the particles 38' instead of imparting roughening to the surface of the balloon, are echogenic or radiopaque. In other embodiments, the particles 38, 38' may be both of a nature which roughens the outer surface of the balloon and which are also echogenic and/or radiopaque. In such an embodiment, thus, the balloon would be both roughened and readily visible by ultrasonic imaging techniques when deployed within a patient.

As with the embodiment of FIG. 1, the embodiment of balloon 16' may have layers 34, 36' which are of the same or similar materials as the balloon 16 of FIG. 1.

The smooth nature of the balloon 16' of the embodiment in FIG. 2, can be achieved in a variety of ways, including by the use of particles 38' which are relatively small compared to the thickness of the layer 36' of the balloon, by the use of a smaller concentration of particles 38' and so on.

Figure 3:
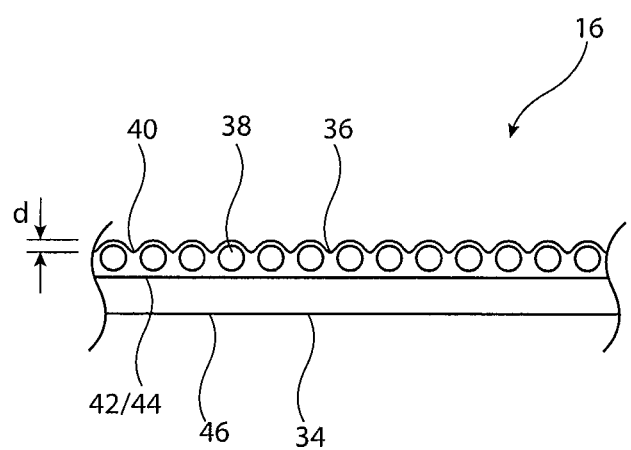
FIG. 3 is an enlarged view of a part of the balloon on the balloon catheter of FIG. 1.

FIG. 3, to which reference is now made, shows an enlarged view of a portion of the balloon 16 of FIG. 1, in particular to depict the structure of the wall of the balloon 16. In this regard, the balloon 16, as described above, includes a roughened or otherwise textured surface 40 forming the outer surface of the balloon 16 and a smooth inner surface 46 of the balloon 16, which is formed by the inner surface of the inner layer 34. The inner and outer layers 34, 36, respectively, have their facing surfaces 42, 44 bonded or otherwise integral with one another, so that the two layers 34, 36 of the balloon 16 are in effect unitary.

The particles 38 embedded within the outer layer 36 are generally round, spherical or cuboidal and preferably made of a material having a higher Durometer compared to the Durometer of the polymeric material which forms the second balloon layer 36. The particles 38 may typically have an average diameter of between 2 to 20 micrometers, more preferably of between 5 to 10 micrometers. A practical example used particles having an average diameter of 7 micrometers. This compares to a thickness for the inner layer 34 of the balloon 16 of between about 0.01 millimeters to 0.10 millimeters that a thickness of the second balloon layer (that is average thickness) in the range of about 0.005 millimeters to about 0.05 millimeters.

With reference in particular to FIG. 3, the roughening of the outer surface 40 of the outer layer 36 of the balloon caused by the particles 38 will produce surface roughening or undulations having an average roughness of around 0.2 to around 18 Ra.

This structure of balloon 16, that is with an inner support layer 34 supporting the particle-containing layer 36, provides optimum strength to the balloon 16, enabling the overall thickness of the balloon wall to be minimized without compromising the strength and therefore performance of the balloon for medical treatments. Moreover, the inner support, layer 34 acts to prevent undue stretching of the balloon 16 and in particular of the outer layer of the balloon 16, which could compromise the integrity of the outer layer and also lead to burst during use. Furthermore, the use of particles 38 to provide roughening of the outer surface 40 of the balloon 16 does not unduly compromise the longitudinal flexibility of the balloon 16, 16', that is its flexibility about the longitudinal axis of the carrier catheter 12.

A convenient method of manufacturing a medical balloon of the type disclosed herein is to commence from a tubing which is then heated and inflated within a mold having mold surfaces consistent with the shape of the final balloon.

Figure 4:
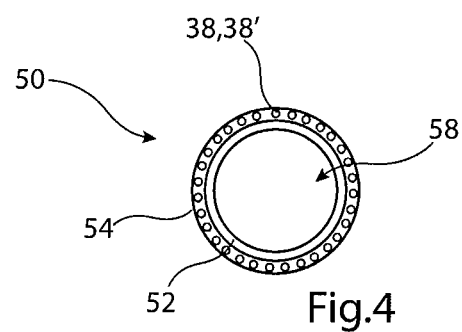
FIGS. 4 to 6 are embodiments of raw tubing for making a medical balloon as taught herein.
Figure 5:
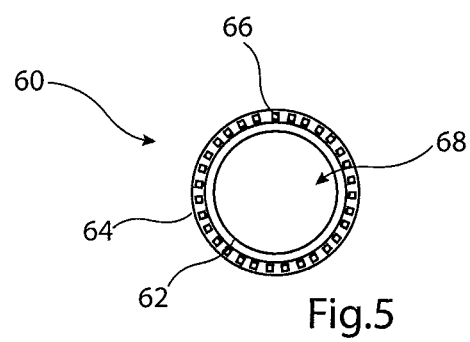
Figure 6:
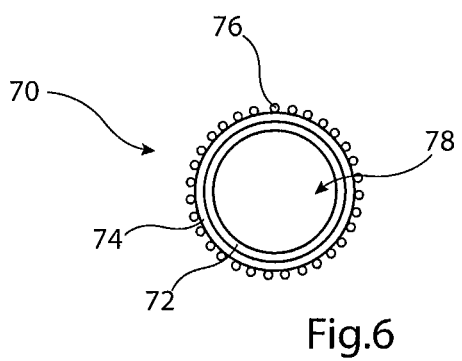

Referring to FIGS. 4 to 6, there are shown different embodiments of raw tubing which are used in the manufacture of a balloon having the characteristics taught herein. The examples of raw tubing in FIGS. 4 to 6 have, as explained below, different characteristics relating particularly to the particles embedded in the outer layer of the balloon. Raw tubing of such nature can conveniently be produced by extrusion, which is a technique also useful in producing multi-layered balloons.

Referring first to FIG. 4, the embodiment of raw tubing 50 shown is intended to produce a balloon 16, 16' of the type shown in FIG. 1 or 2, in dependence upon the particles 38, 38' incorporated within the raw tubing 50. The raw tubing 50 includes an inner layer 52, which forms the inner layer 34 of the balloon 16, 16' and an outer layer 54, which forms the outer layer 36, 36' of the balloon. Embedded within the outer layer 54 are particles 38, 38' which are preferably evenly spread throughout the outer layer 54. In this embodiment, the particles 38, 38' are round, preferably substantially spherical. They thus have the shape shown in FIGS. 1 to 3. It is to be understood that the thickness of the layers 52, 54 will not necessarily be as shown in FIG. 4. In one example, for a 20 mm balloon, the layers 52, 54 will have a thickness of around 0.1 to 0.3 mm and the particles, particularly glass beads, may have an average diameter of approximately 7 micrometers. Of course, once the raw tubing has been inflated, the thickness of the layers 52, 54 will be substantially diminished as a result of stretching, particularly in the region of the body portion 18 of the balloon.

FIG. 5 shows another embodiment of raw tubing 60, also formed of two layers 62, 64. In this instance, there are provided in the layer 64 particles 66 which have a generally cuboidal (square) form. It is preferred, in order to ensure even roughening of the outer surface of the balloon 16, that the particles 66 have a generally square or round form so that they can produce roughening depressions of substantially even depth d, as shown in FIG. 3.

The embodiments of raw tubing shown in FIGS. 4 and 5 provide the particles 38, 38' and 66 already embedded within the outer layer 54. This is not, however, a necessary feature. FIG. 6 shows another example of raw tubing 70, again having inner and outer layers 72 and 74, but in this instance the particles 76 are disposed on the outer surface of the outer layer 74. They may be attached to the outer surface 74, for example by adhesive, fusion or other bonding. This embodiment thus enables the extrusion of a raw tubing having two or more layers, each of which is made of polymeric material with no particulate additive therein. The particles 76, which are subsequently attached to raw tubing 70, become embedded within the outer layer 74 during the balloon formation process, as described below.

FIG. 6 shows particles 76 which are substantially spherical but it is to be understood that these particles could take any other shape, particularly the cuboidal shape of which an example is shown in FIG. 5.

Figure 7:
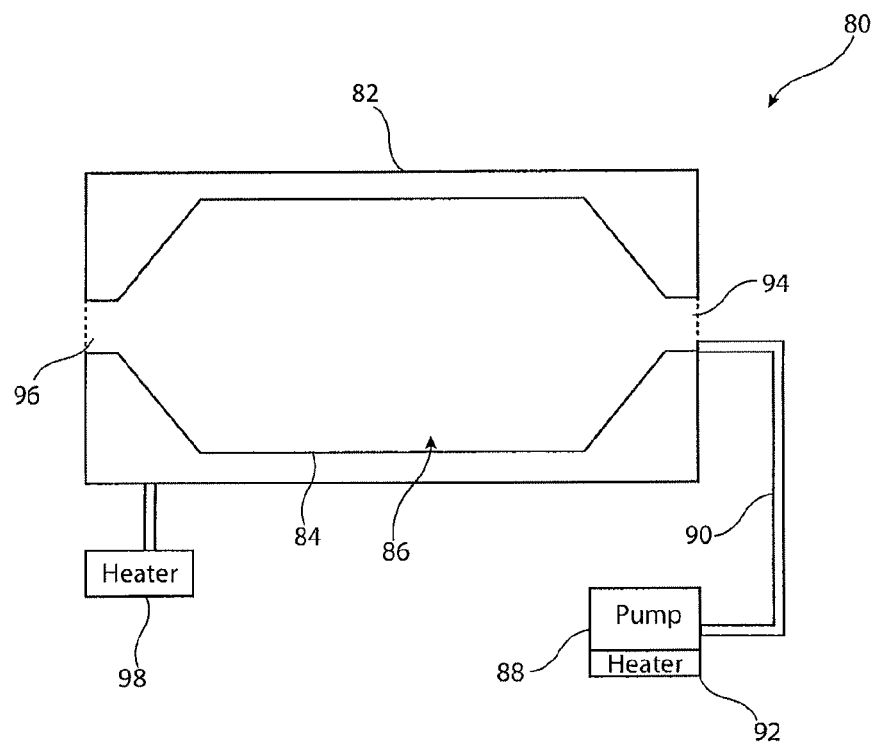
FIG. 7 is a schematic diagram of an embodiment of mold assembly for producing a balloon catheter as taught herein.

Referring now to FIG. 7, there is shown in schematic form an example of mold apparatus 80 for producing a balloon 16, 16' of the type disclosed herein. The apparatus 18 includes a mold unit 82, typically made of metal or ceramic, which has internal walls 84 with a shape consistent with that of the final balloon shape produced by the mold 82. The internal mold walls 84 provide a chamber 86 for receiving the raw tubing 50, 60, 70 at the start of the process. Typically, the mold unit 82 will be made of a plurality of sections which can be separated to remove the balloon 16, 16' after its manufacture.

In addition, the assembly 80 includes a pumping unit 88 coupled to the mold 82 by a suitable fluid conduit 90 and which in practice couples to the internal lumen 58, 68, 78 of the raw tubing 50, 60, 70, respectively. The pump unit 88 typically includes a heater 92 for heating the fluid pumped by the pump 88. Additionally or in the alternative, there may be provided a heater 98 for heating the mold unit 82.

The internal walls 84 of the mold unit 80 include a central cylindrical portion bounded by first and second frusto-conical portions which themselves are coupled to inlet and outlets 94, 96 of the mold unit 82. The inlet and outlet 94, 96 are of a diameter able to accommodate the raw tubing 50, 60, 70 therethrough and they include one or more clamps (not shown) to fix the raw tubing to the mold 82 during the balloon production process, although clamps are not essential.

The balloon 16, 16' may be formed by the raw tubing 50-70 as follows. The raw tubing 50-70 is, in the preferred embodiment, of continuous form, that is has no variation along its length in terms of the size and structure of the various layers of the balloon. It is not excluded, however, that the raw tubing 50-70 could have different characteristics in the zones which are to produce the end cones and necks of the balloon.

A length of raw tubing is inserted in the mold unit 82, through the inlet 94, and out of the outlet 96. If not already cut, the raw tubing is then cut to leave very short sections extending out of the mold unit 82. The end of the raw tubing 50-70 which extends out of the outlet 96 is sealed by closing off its internal lumen 58-78. The conduit 90 is then coupled to the other end of the raw tubing 50-70 extending out of the inlet 94, this being a fluid-tight coupling of the conduit 90 supplying inflation fluid to the lumen 58-78. The heater or heaters 90/98 are then operated to heat the fluid (typically a gas) and/or mold 82 which is pumped under pressure into the raw tubing 50-70. The combination of fluid pressure and heat causes the raw tubing 50-70 to soften and expand into the chamber 86 until it comes into abutment with the internal walls 84 of the mold unit 82, thus attaining the balloon shape 16, 16'. So doing causes the layers of the raw tubing 50-70 to stretch and thus become thinner during the inflation process. In the case where the particles 38, 66, 76 create a roughing of the outer surface of the balloon 16, the stretching of the outer layer 54, 64, 74 of the raw tubing will cause this to expose the shape of the particles 38, in a manner akin to the drawing of FIG. 3. The polymeric material of the outer layer 54-74 of the raw tubing is such as to retain the particles 38, 66, 76 embedded therewithin and thus to ensure that the balloon 16 retains a unitary characteristic.

The inner layer 52-72, while also stretching under the effects of pressure and heat, being a stronger layer than the outer layer 54-74 will continue to support the outer layer 54 and will retain a generally smooth outer surface 44. It is not excluded that the inner layer 52-72 may fit around the shape of the particles 38 when in the mold 82 as a result of the hardness of the mold 72 but when the balloon 16 is subsequently inflated during this deployment, the inner layer 34 of the balloon 16 will remain substantially flat so as to produce and/or retain the surface roughening or texturing. Having an inner layer 52-72 made of material which has a higher softening temperature than that of the outer layer 54-74 will assist in achieving these characteristics.

The embodiment of balloon of FIG. 2 can be formed in the same manner as described above, although in this instance as a result of the size of the particles with respect to the thickness of the outer layer of the balloon 16' once inflated, the particles will not substantially alter the smoothness of the outer surface of the outer layer 38' of the balloon 16'. In this embodiment, the particles 38' provide only an echogenic and/or radiopaque function.

It will be appreciated that the particles 38, 38' will not, in the preferred embodiment, alter their shape during this molding process primarily as a result of these particles being made of a material having a higher softening or melting temperature than that of the layers 52, 54 of the raw tubing and also of the temperature to which the mold unit 82 is heated.

With respect to the embodiment of raw tubing of FIG. 6, again the method of molding is the same as that for the raw tubing of FIGS. 4 and 5. As the raw tubing 70 is inflated and heated in the mold 82, the particles 76 remain on the outside of the outer layer 74, until they become pressed against the internal walls 84 of the mold 82. At this point, as the result of the softening of the outer layer 74, the material of the outer layer 74 will flow around the particles 76 until the particles 76 are substantially embedded within the material 74, which will form the outer layer 36 of the balloon 16. It is to be understood that the particles 76 could either be roughening particles as in the embodiments of FIGS. 1 and 3 or particles which do not contribute to roughening of the outer surface of the balloon, as in the embodiment of FIG. 2.

In another embodiment there is provided a raw tubing which is formed only of layers of polymeric material, that is without any particles provided in or on the raw tubing. In this embodiment, the particles are located within the mold cavity 86, preferably temporarily attached to the internal walls 84 of the mold 82. In this embodiment, when the raw tubing is heated and inflated, this will stretch until it presses against the internal walls 84, in so doing taking up the particles into the outer layer of the raw tubing and thus into what becomes the outer layer of the finished balloon.

The particles may be granules, pellets, spheroids and could be solid or hollow. If they are hollow, they could be filled with a gas or fluid, such as to improve the radiopacity or echogenicity of the particle and thus of the balloon within which they are embedded.

With reference again to FIG. 1, a balloon 16 having a roughened surface of the type shown in this Figure can substantially enhance the positional stability of the balloon 16 when in a patient. This is particularly important in a number of medical procedures such as valvuloplasty, occlusion and the like, where a balloon with a smooth outer surface can easily slip. A balloon with a roughened outer surface can also be advantageous in retaining a balloon expandable medical device such as a stent or stent graft on the balloon during deployment of the device.

The particles may only be partially embedded in the balloon wall, particularly in the case of a balloon formed of at least two layers.

It will be appreciated that the balloon could be formed with a wall having more than two layers and could have a different shape to the shape shown in the drawings and discussed above.

It is to be understood that the features of the different embodiments described can be combined with one another and that the claims are to be interpreted, even though initially set out in single dependent form, as being combinable as if in multiple dependent form.

What is claimed is:

1. A non-compliant medical balloon for endoluminal location within a patient, the balloon including a first balloon layer made of a polymeric material, and a second balloon layer overlying the first balloon layer, wherein the second balloon layer includes a polymeric material comprising generally spherical or cuboidal particles embedded and evenly distributed therewithin, wherein the particles create a roughened outer surface to the balloon, the roughened outer surface being configured to prevent movement of the balloon relative to an engaged bodily tissue, wherein the polymeric material of the second balloon layer has a lower softening or melting temperature than the softening or melting temperature of the material of the first balloon layer, and wherein the particles are made of a material having a higher softening or melting temperature compared to the softening or melting temperature of the polymeric materials of both the first balloon layer and the second balloon layer.

2. A medical balloon according to claim 1, wherein the particles have an average diameter of between 2 to 20 micrometers.

3. A medical balloon according to claim 2, wherein the particles have an average diameter of between 5 to 10 micrometers.

4. A medical balloon according to claim 3, wherein the particles have an average diameter of 7 micrometers.

5. A medical balloon according to claim 1, wherein the first balloon layer has a thickness in the range of 0.01 millimeters to 0.10 millimeters.

6. A medical balloon according to claim 1, wherein the second balloon layer has a thickness in the range of 0.005 millimeters to 0.05 millimeters.

7. A medical balloon according to claim 1, wherein an outer surface of the balloon has a roughness of 0.2 to 18 Ra.

8. A medical balloon according to claim 1, wherein the particles are provided at a density of 50 to 80% by weight or 3 to 5% by volume of the second layer of the balloon.

9. A medical balloon according to claim 1, wherein the particles are made of a material having a higher Durometer compared to the Durometer of the polymeric material of the second balloon layer.

10. A medical balloon according to claim 1, wherein the particles are made of one or more of glass, metal, a polymer, ceramic, tungsten, and carbon.

11. A medical balloon according to claim 1, wherein the polymeric material of the first balloon layer includes one or more of polyamide, polyether block amide, PET, polyethylene and polyurethane.

12. A medical balloon according to claim 1, wherein the second balloon layer covers the entirety of an inflatable portion of the balloon.

13. A medical balloon according to claim 1, wherein the first and second balloon layers are co-extruded, fused or bonded to one another.

14. A medical balloon according to claim 1, wherein said particles comprise a radiopaque or echogenic material.

15. A medical balloon catheter provided with a medical balloon disposed on an elongate catheter, the medical balloon comprising a first balloon layer made of a substantially non-compliant polymeric material, and a second balloon layer overlying the first balloon layer, wherein the second balloon layer comprises a polymeric material comprising generally rounded, spherical or cuboidal particles embedded and evenly distributed therewithin, said particles creating a uniformly roughened atraumatic outer surface to the balloon configured to prevent movement of the balloon relative to engaged bodily tissue; said balloon being configured for use in one of angioplasty, vascular dilatation, occlusion, valvuloplasty and device deployment.

16. A balloon catheter including a medical balloon according to claim 1.

* * * * *